(12) United States Patent
Weinberg

(10) Patent No.: US 8,163,002 B2
(45) Date of Patent: Apr. 24, 2012

(54) SELF-SEALING VASCULAR GRAFT

(75) Inventor: Steven Weinberg, League City, TX (US)

(73) Assignee: Vascular Devices LLC, North Brunswick, NJ (US)

( * ) Notice: Subject to any disclaimer, the term of this patent is extended or adjusted under 35 U.S.C. 154(b) by 230 days.

(21) Appl. No.: 11/517,683

(22) Filed: Sep. 8, 2006

(65) Prior Publication Data

US 2007/0123968 A1    May 31, 2007

Related U.S. Application Data

(60) Provisional application No. 60/736,385, filed on Nov. 14, 2005.

(51) Int. Cl.
*A61F 2/06* (2006.01)
(52) U.S. Cl. ........................................... 623/1.13
(58) Field of Classification Search ........... 623/1.13, 623/1.1, 1.4
See application file for complete search history.

(56) References Cited

U.S. PATENT DOCUMENTS

| | | | |
|---|---|---|---|
| 3,105,492 A | 10/1963 | Jeckel | |
| 3,814,137 A * | 6/1974 | Martinez | 138/103 |
| 4,130,904 A * | 12/1978 | Whalen | 623/1.44 |
| 4,193,138 A | 3/1980 | Okita et al. | |
| 4,229,838 A | 10/1980 | Mano et al. | |
| 4,581,390 A * | 4/1986 | Flynn | 523/112 |
| 4,619,641 A | 10/1986 | Schanzer | |
| 4,816,339 A * | 3/1989 | Tu et al. | 428/421 |
| 4,850,999 A | 7/1989 | Planck et al. | |
| 5,061,276 A | 10/1991 | Tu et al. | |
| 5,084,065 A | 1/1992 | Weldon et al. | |
| 5,100,422 A * | 3/1992 | Berguer et al. | 606/151 |
| 5,116,360 A * | 5/1992 | Pinchuk et al. | 623/11.11 |
| 5,192,310 A | 3/1993 | Herweck et al. | |
| 5,453,235 A | 9/1995 | Calcote et al. | |
| 5,584,876 A | 12/1996 | Bruchman et al. | |
| 5,607,463 A | 3/1997 | Schwartz et al. | |
| 5,628,782 A | 5/1997 | Myers et al. | |
| 5,674,272 A | 10/1997 | Bush et al. | |
| 5,700,287 A | 12/1997 | Myers et al. | |
| 5,716,395 A | 2/1998 | Myers et al. | |
| 5,749,880 A | 5/1998 | Banas et al. | |
| 5,800,512 A | 9/1998 | Lentz et al. | |
| 5,866,217 A | 2/1999 | Stenoien et al. | |
| 5,910,168 A * | 6/1999 | Myers et al. | 623/1.44 |
| 5,931,865 A * | 8/1999 | Silverman et al. | 138/103 |
| 5,976,192 A | 11/1999 | McIntyre et al. | |
| 6,036,724 A | 3/2000 | Lentz et al. | |
| 6,080,198 A | 6/2000 | Lentz et al. | |
| 6,180,059 B1 | 1/2001 | Divino, Jr. et al. | |
| 6,187,039 B1 | 2/2001 | Hiles et al. | |

(Continued)

OTHER PUBLICATIONS

Credent Vascular Technologies, Challenging Traditional Artificial Grafts, http://www.lemaitre.com/credent/products.htm.

*Primary Examiner* — S. Thomas Hughes
*Assistant Examiner* — Julie A Szpira
(74) *Attorney, Agent, or Firm* — Lerner, David, Littenberg, Krumholz & Mentlik, LLP

(57) ABSTRACT

The present invention relates to a segmental self-sealing graft for implantation in a patient including a base tubing element, a tubular access element overlying the base tubing, and a strand-like compression element wound over the access element so as to provide radially inward compression, and a method of making same.

18 Claims, 4 Drawing Sheets

U.S. PATENT DOCUMENTS

| | | |
|---|---|---|
| 6,261,257 B1 | 7/2001 | Uflacker et al. |
| 6,283,991 B1 | 9/2001 | Cox et al. |
| 6,287,337 B1 | 9/2001 | Martakos et al. |
| 6,319,279 B1 * | 11/2001 | Shannon et al. ............. 623/1.44 |
| 6,358,284 B1 | 3/2002 | Fearnot et al. |
| 6,428,571 B1 | 8/2002 | Lentz et al. |
| 6,454,997 B1 | 9/2002 | Divino, Jr. et al. |
| 6,521,284 B1 | 2/2003 | Parsons et al. |
| 6,540,780 B1 | 4/2003 | Zilla et al. |
| 6,582,387 B2 | 6/2003 | Derek et al. |
| 6,582,409 B1 | 6/2003 | Squitieri |
| 6,673,102 B1 | 1/2004 | Vonesh et al. |
| 6,676,900 B1 | 1/2004 | Divino, Jr. et al. |
| 6,719,783 B2 | 4/2004 | Lentz et al. |
| 6,743,218 B2 | 6/2004 | Maginot et al. |
| 6,863,686 B2 | 3/2005 | Shannon et al. |
| 6,902,556 B2 | 6/2005 | Grimes et al. |
| 6,939,377 B2 | 9/2005 | Jayaraman et al. |
| 7,244,271 B2 * | 7/2007 | Lentz et al. .................. 623/1.44 |
| 7,244,272 B2 * | 7/2007 | Dubson et al. ............... 623/1.44 |
| 2002/0111667 A1 | 8/2002 | Girton et al. |
| 2003/0004559 A1 | 1/2003 | Lentz et al. |
| 2003/0083737 A1 | 5/2003 | Greene et al. |
| 2003/0100944 A1 | 5/2003 | Laksin et al. |
| 2004/0099395 A1 | 5/2004 | Wang et al. |
| 2004/0193242 A1 * | 9/2004 | Lentz et al. .................. 623/1.4 |
| 2004/0215337 A1 * | 10/2004 | Hain et al. .................... 623/1.44 |
| 2006/0058867 A1 * | 3/2006 | Thistle et al. ................ 623/1.13 |
| 2007/0088336 A1 | 4/2007 | Dalton |
| 2008/0027534 A1 * | 1/2008 | Edwin et al. ................. 623/1.44 |

* cited by examiner

SELF-SEALING VASCULAR GRAFT

CROSS-REFERENCE TO RELATED APPLICATIONS

This application claims the benefit of the filing date of U.S. Provisional Patent Application No. 60/736,385 filed Nov. 14, 2005, the disclosure of which is hereby incorporated herein by reference.

BACKGROUND OF THE INVENTION

Grafts, for example hemodialysis grafts, are often used for patients who need to receive frequent injections, blood filtration, or vascular access procedures. For example, patients who receive kidney dialysis typically received several treatments per week. In order for the patient to receive treatment, the patient's skin must be punctured with a hemodialysis needle. Such needles are typically about 15-17 gauge, and they leave a puncture which takes some time to heal. With the frequency of dialysis treatments, puncture wounds accumulate, and there is a danger of undermining the patient's veins.

It has become common to implant a graft in the patient's arm to receive the punctures. Typically, the graft is a tubular member which is implanted in the patient's forearm, although other locations may be used. The graft is connected between two spaced points in the circulatory system. In the past, veins from animals were used as the graft material, but today it is common to use an artificial material, such as polymer tubing. However, the punctures in such tubing tend to leak under the pressure of the circulatory system. In all cases, the graft can not be used immediately and must be allowed to heal-in or mature, before it can be punctured. Efforts have been made to use tubes made of a self-sealing polymer or to provide a multilayered structure to resolve these problems; but such grafts have not been proven to be a reliable solution to long term patency.

It would therefore be desirable to provide a graft made of an artificial material which can reliably prevent blood leakage from repeated punctures when in use. Preferably, it should be relatively simple in construction, made of medically accepted and biologically compatible materials, and its implantation and use should be no more complicated than the existing grafts.

SUMMARY OF THE INVENTION

In accordance with an embodiment of the present invention, an artificial graft includes a base tubing element, a tubular access element overlying the base tubing, and a compression element formed over the access element so as to provide radially inward compression thereto. The compression element may be a strand-like compression element wound over the access element. The base tubing element is preferably made of a polymer, such as expanded polytetrafluoroethylene (ePTFE), a material which is commonly approved for surgical and medical purposes. The tubular access element is preferably made of a material which exhibits self-sealing properties, such as by way of one example, a gum silicone elastomer, which is preferably bonded to the base tubing surface. The compression element may be a polytetrafluoroethylene (PTFE) tape or yarn, which may be helically wound about the exterior of the access element in order to provide radial compression of the access element and improve its leakage resistance. The compression element may also be a biocompatible silicone layer molded directly over the access element so as to provide sufficient radial compression of the access element to improve its leakage resistance.

It is a feature of one aspect of the present invention that a compression member formed about the access element improves the leakage resistance of the access element after it has been punctured by applying radially inward pressure. The compression member may be a strand-like compression member wound about the access element or a biocompatible silicone layer formed over the access element.

It is a feature of one aspect of the present invention that an artificial graft is constituted of a tubular base element, an overlying sleeve-like access element made of a material exhibiting self-sealing properties upon being punctured and mounted in contact with the base element, and a compression member formed about the access element so as to provide sufficient radial compression thereto to improve the leakage resistance of the graft after being punctured. The compression element may be a strand-like compression element wound over the access element or a biocompatible silicone layer formed over the access element.

It is a feature of an aspect of the present invention that an artificial graft is constituted of a tubular base element made of ePTFE, an overlying sleeve-like access element made of a gum silicone material or other suitable elastomer exhibiting self-sealing properties upon being punctured and molded on the base element, and a compression band or tape member having a width which avoids being severed when pierced by a hemodialysis needle, such as a spiral or helical band wound about the access element so as to provide sufficient radial compression thereto to improve the leakage resistance of the graft after being punctured. The transition of the silicone segment from the ePTFE tubing provides for smooth surgical tunneling of the graft. It is also contemplated that a biocompatible silicone layer could be molded over the access element and compression member so as to enclose them and to provide sealing properties. This outer layer may be microporous or contain a textured outer surface to enhance tissue healing and graft stabilization.

It is a feature of an aspect of the present invention that an artificial graft is constituted of a tubular base element made of ePTFE, an overlying sleeve-like access element made of a gum silicone material or other suitable elastomer exhibiting self-sealing properties upon being punctured and molded on the base element, and a biocompatible silicone layer formed over the access element so as to provide sufficient radial compression of the access element to improve its leakage resistance after being punctured.

BRIEF DESCRIPTION OF THE DRAWINGS

The foregoing brief description and further objects, features, and advantages of the present invention will be understood more completely from the following detailed description of presently preferred, but nonetheless illustrative, embodiments in accordance with the present invention, with reference being had to the accompanying drawings in which.

DETAILED DESCRIPTION

Figure 1:
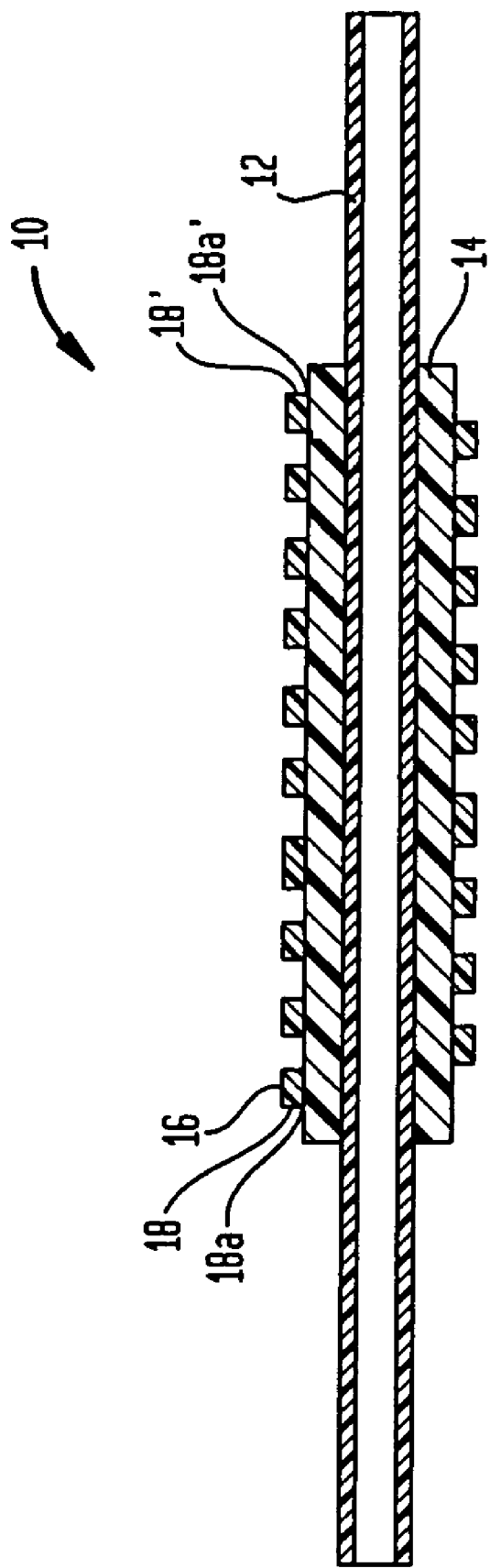
FIG. 1 is a longitudinal cross sectional view of one embodiment of an artificial graft in accordance with the present invention, showing the internal construction thereof.

Turning now to FIG. 1, graft 10 broadly comprises a base tubing element 12, a tubular access element 14 overlying the base tubing element, and a compression element 16 wound over the access element so as to provide radially inward compression thereto.

Base tubing element 12 preferably has a circular cross-section but it may have any cross-sectional shape commonly used for surgical and implantation applications. Base tubing element 12 is preferably made of implant grade ePTFE tubing having an inside diameter of, by way of preferred example only, about 6.0 mm and a wall thickness of about 0.5 mm. Preferably the graft 10 is provided in a fixed length, usually longer then required and cut by a surgeon, for example to the length of base tubing element 12, which is convenient for implantation, for example about 13.5 cm. However, tubing element of other length, diameter and wall thickness will work equally well, as will be appreciated by those skilled in the art. Tubing made of ePTFE is preferred for element 12 because this material has enjoyed wide application in medicine and surgery, particularly for implant applications. However, those skilled in the art will appreciate that tubing made of other biocompatible materials approved for implant applications may work equally well, such as tubing made of polyurethane or polyester and the like.

The graft 10 will have one or more access elements 14. Typically, most grafts would have two access elements—one for removal of untreated blood and one for the return of filtered blood, but those skilled in the art will appreciate that there may be some instances in which it would be convenient to provide additional access elements. In this regard, the access elements 14 may be positioned adjacent one another about the tubing element 12. Notwithstanding the foregoing, the invention contemplates a single access element 14 for removal and return of blood.

Preferably, access element 14 is made of implant grade, platinum-cured gum silicone elastomeric material. It is preferred that this elastomeric material has a 20-35 Shore durometer hardness (NuSil MED-4020/4035 or equivalent). However, other self-sealing materials will also work well, such as urethane or other biocompatible elastomers. In any event, the material should be biocompatible, capable of withstanding multiple punctures with minimal leakage, and sufficiently soft to permit a medical practitioner to pierce it without using undue force. Other materials that could be used include gum and liquid silicone rubber, polyether or polycarbonate based polyurethanes. It is also contemplated that access element 14 have a wall thickness of approximately about 0.3 mm to about 1.5 mm, and preferably about 0.5 to about 1.0 mm.

In the preferred embodiment, access element 14 is compression molded or liquid injection molded onto the outside of base tubing element 12. This is preferably done by placing tubing element 12 on a mandrel that has the same outside diameter as the inside diameter of the tubing element. A mold is then placed around the tubing element 12 and liquid or gum silicone is introduced into the mold at a pressure which is preferably in the range of about 200 to about 300 psi. Alternatively, the access element 14 may be formed as a gum silicone sheet material and partially cured. It can then be applied over tubing element 12, a two part mold applied around it and compressed in a 7-8 ton press at a temperature of about 200° F. In order to improve the adhesion of the access element 14, the outside surface of that portion of tubing element 12 underlying the access element or the interior surface of access element may be subjected to surface activation such as by applying a chemical treatment or physical treatment (e.g. abrasion) to ensure that the bond between elements 12 and 14 is secure and lasting, so that the two elements will not separate in use. An access element 14 with the above composition will exhibit self-sealing properties. That is, when access element 14 is punctured with a fine point, such as a hemodialysis needle, it will tend to close up the puncture when the needle is removed.

It has been found that, upon being pierced by a needle, a non-coated tubing element 12 develops a tiny inwardly hanging tab at the site of the puncture. As the graft 10 may be punctured several times per week, leakage will occur through the opening left by this hanging tab. The molding pressure for access element 14 was selected to be relatively high so as to assure that the silicone material forming access element 14 works into the surface pores of tubing element 12. As a result, it is contemplated that after a piercing needle is withdrawn, the resilience of access element 14 causes the hanging tab to be drawn up into the puncture in tube element 12 to block it. By minimizing or eliminating the hanging tab, blood flow through the graft lumen will not be impeded.

Compression element 16 is preferably a strand-like elongated member which can be wound about access element 14 to provide radially inward compression to improve the leak resistance of that element after it is punctured. Preferably, compression element 16 is made of a yarn in tape form, most preferably a tape or band material generally available in the form of PTFE tape. However, other forms of the compression element 16 other than tape, such as round, oval, square and the like are within the scope of the invention. It is preferred that the width of compression element 16 be such that, with the intended gauges of needles to be used, element 16 may be pierced without being severed. Preferably, compression element 16 is wound with a tension approximately in the range of about 10 to about 300 grams, most preferably about 40 grams. However, any tension will be effective which causes a increase in the self-sealing ability of access element 14 but does not cause the tubing element 12 to collapse.

Figure 2A:
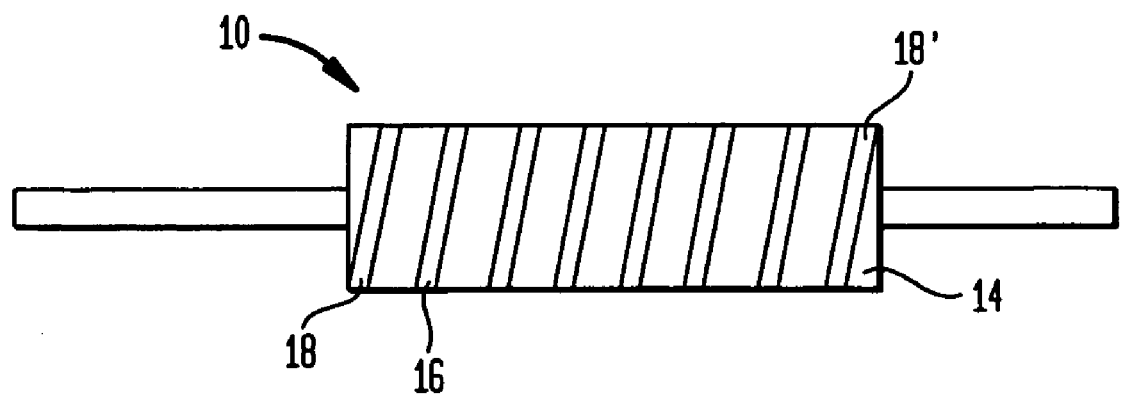
FIG. 2A is a side elevational view of the artificial graft of FIG. 1 showing a helically wound compression element.

As may be seen in FIGS. 1 and 2A, compression element 16 is secured at location 18 near one end of access element 14 and is thereafter wound about access element 14, preferably in a helical or spiral pattern which advances about 1.5 mm per rotation. When the other end of access element 14 is reached, the compression element 16 is once again secured to it at location 18'. Preferably, the securement of compression element 16 at locations 18 and 18' is achieved by some suitable means, such as forming slits 18a, 18a' in access element 14 at locations 18, 18', respectively, and inserting an end of compression element 16, after which the end of compression element 16 is bonded in place, preferably by means of an RTV (Room Temperature Vulcanizing) adhesive. Those skilled in the art will appreciate that other biocompatible bonding materials may be used, such as cyanoacrylate. The ends of compression element 16 could alternately be secured by other methods, such as being tied off to the access element 14 and knotted.

Figure 2B:
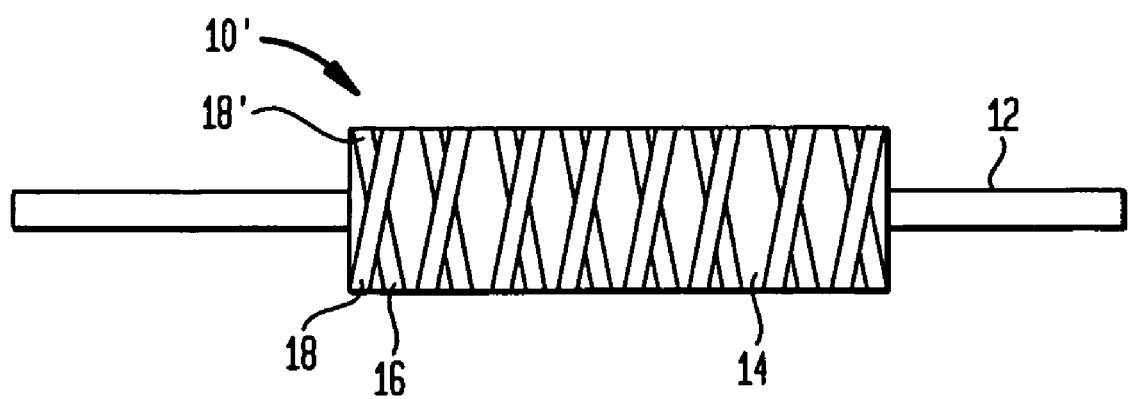
FIG. 2B is a side elevational view of another embodiment an artificial graft in accordance with the present invention showing a compression element that is wound in the pattern of a double helix.

In an alternate embodiment 10', which is illustrated in FIG. 2B, compression element 16 is secured at the first end 18 of access element 14, as above, is wound in a helical pattern towards the second end 18' of access element 14, and is then wound in a helical pattern back towards the first end of access element 14 so as to cross the previous windings. When the first end 18 of access element 14 is reached, the end of compression element 16 is once again secured to it, as above. In this double helix pattern, the compression element 16 preferably advances about 2 mm per rotation.

Figure 3:
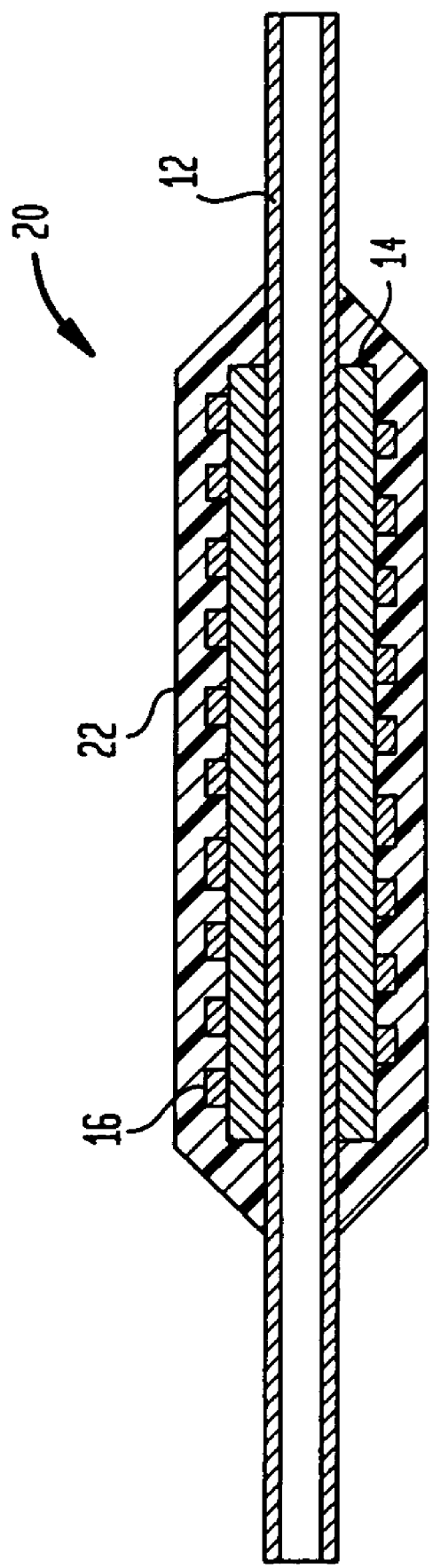
FIG. 3 is a longitudinal cross sectional view of still another embodiment of an artificial graft in accordance with the present invention showing the internal construction thereof, wherein a biocompatible silicone layer is formed over the access element and compression member.

FIG. 3 illustrates a third embodiment of an artificial graft 20 in accordance with the present invention. This embodiment is similar to embodiments 10 and 10' in FIGS. 1, 2A and 2B except that an outer covering 22 is provided over compression element 16 in the structures. In FIG. 3, those elements which are identical to elements in FIG. 1 have been indicated with the same reference numbers.

Preferably, the covering 22 is made of platinum-cured silicone gum or a liquid silicone with a durometer hardness of 20-35 Shore A (NuSil MED-4035 or equivalent). This material is compression molded on the structure after compression element 16 has been secured, in a manner similar to access element 14. In the preferred embodiment, covering 22 has a wall thickness of about 0.25 to about 0.5 mm. It is also preferred that cover 22 have an exterior surface #45 "texturing" (Charmilles Technologies, VDI 3400), or a micro-porosity (50 to 200 microns) providing an environment to allow for biological connective material attachment and to assist in the long term stability of the graft 20 within the patient's subcutaneous tissue. Except for its durometer, this material can be made of the same material as access element 14. However, those skilled in the art will appreciate that cover 22 need not be made of the same material as access element 14. Alternate materials that could be used include biocompatible elastomers such as polyurethane.

Figure 4:
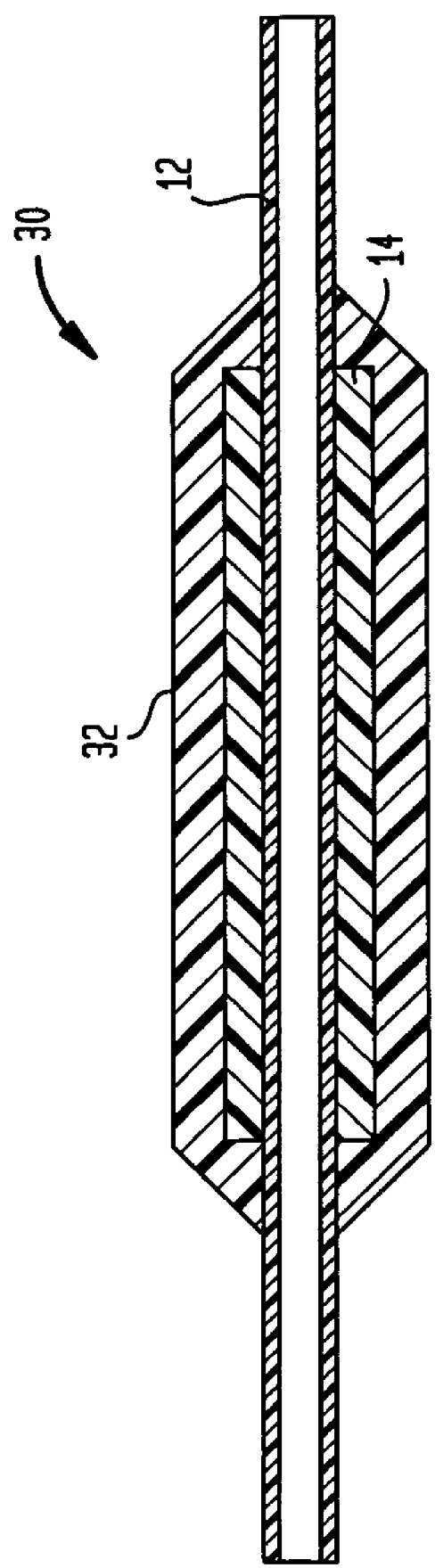
FIG. 4 is a longitudinal cross sectional view of another embodiment of an artificial graft in accordance with the present invention showing the internal construction thereof, wherein a biocompatible silicone layer is formed directly over the access element.

FIG. 4 illustrates a fourth embodiment of an artificial graft 30 in accordance with the present invention. Graft 40 broadly comprises a base tubing element 12, a tubular access element 14 overlying the base tubing, and an outer covering 32 formed over access element 14 so as to provide radial compression to the access element. In the embodiment illustrated, the covering 32 may extend past the extent of the access element 14 and about a portion of the tubing element.

Base tubing element 12 preferably has a circular cross-section but it may have any cross-sectional shape commonly used for surgical and implantation applications. Tubing element 12 is preferably made of implant grade ePTFE tubing having an inside diameter about 6.0 mm and a wall thickness of about 0.5 mm. Preferably the graft 30 is provided in a fixed length, usually longer then required and cut by surgeon, for example to the length of base tubing element 12, which is convenient for implantation, for example about 30 cm. However tubing element 12 of other length, diameter and wall thickness will work equally well, as will be appreciated by those skilled in the art. Tubing made of ePTFE was selected for tubing element 12 because this material has enjoyed wide application in medicine and surgery, particularly for implant applications. However, those skilled in the art will appreciate that tubing made of other biocompatible materials approved for implant applications may work equally well, such as tubing made of polyurethane or polyester and the like.

There may be one access element 14. However, most grafts would have two access elements—one for removal of untreated blood and one for the return of filtered blood, but those skilled in the art will appreciate that there may be some instances in which it would be convenient to provide additional access elements. In this regard, the access elements 14 may be portioned adjacent one another about the tubing element 12. Notwithstanding the foregoing, the invention contemplates a single access element 14 for removal and return of blood.

Preferably, access element 14 is made of implant grade, platinum-cured gum silicone elastomeric material. It is preferred that this elastomeric tubing has a 20-35 Shore A durometer hardness (NuSil MED-4020/4035 or equivalent). However, other self-sealing materials will also work well, such as urethane or other biocompatible elastomers. In any event, the material should be biocompatible, capable of withstanding multiple punctures with minimal leakage, and sufficiently soft to permit a medical practitioner to pierce it without using undue force. Other materials that could be used include gum and liquid silicone rubber, polyether or polycarbonate based polyurethanes. It is also preferred that access element 14 have a wall thickness of about 0.3 mm to about 1.5 mm, and preferably about 0.5 to about 1.0 mm.

In this embodiment, access element 14 is compression molded or liquid injection molded onto the outside of base tubing element such a previously described. This is preferably done by placing tubing element 12 on a mandrel that has the same outside diameter as the inside diameter of the tubing. A mold is then placed around the tubing element 12 and liquid or gum silicone is introduced into the mold at a pressure which is preferably in the range of about 200 to about 300 psi. Alternately, the access element 12 may be formed as a gum silicone sheet material and partially cured. It can then be applied over tubing element 12, a two part mold is applied around it, and it is compressed in a 7-8 ton press at a temperature of about 200° F. In order to increase the adhesion of the access element 14, the outside surface of that portion of tubing element 12 underlying the access element 14 may be subjected to surface activation such as applying a chemical treatment or physical treatment (e.g. abrasion) to ensure that the bond between elements 12 and 14 is secure and lasting, so that the two elements will not separate in use. An access element 14 with the above composition will exhibit self-sealing properties. That is, when access element 14 is punctured with a fine point, such as a hemodialysis needle, it will tend to close up the puncture when the needle is removed.

In this embodiment, covering 32 also acts as a compression element, applying sufficient inward radial compression to provide an increase in the self-sealing ability of access element 14, without causing the tubing element 12 to collapse.

Preferably, the covering 32 is made of platinum-cured silicone gum or a liquid silicone with a durometer hardness of 20-35 Shore A (NuSil MED-4035 or equivalent). This material is compression molded or liquid injection molded about the access element 14, and optionally about a portion of the tubing element 12, in a manner similar to access element 14 as described with respect to FIG. 1. In this embodiment, covering 32 has a wall thickness of approximately 0.25 to 0.5 mm. It is also preferred that cover 32 have an exterior surface #45 "texturing" (Charmilles Technologies, VDI 3400), or a micro-porosity (50 to 200 microns) providing an environment to allow for biological connective material attachment and to assist in the long term stability of the graft 30 within the patient's subcutaneous tissue. Except for its durometer, this material is made of the same as the material comprising access element 14. Those skilled in the art will appreciate that cover 32 need not be made of the same material as access element 14. Alternate materials that could be used include biocompatible elastomers such as polyurethane.

Although preferred embodiments of the invention have been disclosed for illustrative purposes, those skilled in the art will appreciate that many additions, modifications, and substitutions are possible without departing from the scope and spirit of the invention.

The invention claimed is:

1. A self-sealing vascular graft for implantation in a patient comprising:
    a base tubing element of a biocompatible material,
    at least one tubular access element overlying said base tubing element, wherein said access element is made of a biocompatible material and said base tubing element and said access element are adhered to each other over substantially the entire length of said access element so they do not delaminate when punctured, wherein said access element is a homogeneous continuous structure over substantially the entire length of said access element, and
    a compression element of a biocompatible material surrounding said tubular access element, said compression element providing radially inward compression about said access element sufficient to increase the self-sealing ability of said access element without causing said base tubing element to collapse, wherein said compression element is a homogeneous continuous structure over substantially the entire length of said compression element.

2. The self-sealing vascular graft of claim 1, wherein said biocompatible material for said base tubing element is polyurethane or polyester.

3. The self-sealing vascular graft of claim 1, wherein said biocompatible material for said base tubing element is expanded polytetrafluoroethylene.

4. The self-sealing vascular graft of claim 1, wherein said access element is comprised of two access elements, wherein one of said two access element is adapted for removal of untreated blood and the other access element is adapted for the return of filtered blood.

5. The self-sealing vascular graft of claim 1, wherein said biocompatible material for said access element is selected from the group consisting of a gum silicone elastomer, liquid silicon elastomer, polyether based polyurethane, polycarbonate based polyurethane, polyurethane and urethane.

6. The self-sealing vascular graft of claim 1, wherein said biocompatible material for said access element is a platinum-cured gum silicone elastomer.

7. The self-sealing vascular graft of claim 1, wherein said access element has a wall thickness of about 0.3 mm to about 1.5 mm.

8. The self-sealing vascular graft of claim 1, wherein said access element has a wall thickness of about 0.5 mm to about 1.0 mm.

9. The self-sealing vascular graft of claim 1, wherein said biocompatible material for said compression element is selected from the group consisting of a platinum cured silicone gum elastomer, liquid silicone elastomer, polyether based polyurethane, polycarbonate based polyurethane, polyurethane, and urethane.

10. The self-sealing vascular graft of claim 1, wherein said compression element has a durometer hardness of about 20 to about 35 Shore A.

11. The self-sealing vascular graft of claim 1, wherein the wall thickness of said compression element is from about 0.25 mm to about 0.55 mm.

12. The self-sealing vascular graft of claim 1, wherein the exterior surface of said compression element is microporous or textured.

13. The self-sealing vascular graft of claim 1, wherein said biocompatible material for said base tubing element is expanded polytetrafluorethylene; said biocompatible material for said access element is a platinum-cured gum silicone elastomer; and said biocompatible material for said compression element is a platinum cured silicone gum elastomer.

14. The self-sealing vascular graft of claim 13, wherein said access element has a wall thickness of about 0.33 mm to about 1.5 mm; and said compression element has a wall thickness of about 0.25 mm to about 0.55 mm, wherein the exterior surface of said compression element is microporous or textured.

15. The self-sealing vascular graft of claim 1, wherein the biocompatible material of said access element is worked in surface pores of the base tubing element.

16. A self-sealing vascular graft for implantation in a patient produced by steps comprising:
    providing a base tubing element of biocompatible material,
    adhering at least one tubular access element of biocompatible material to the exterior surface of said base tubing element over substantially the entire length of said access element by compression molding or liquid injection molding technique so that said base tubing element and said access element do not delaminate when punctured, wherein said access element is a homogeneous continuous structure over substantially the entire length of said access element,
    providing a compression element of a biocompatible material over the exterior surface of said at least one tubular access element, said compression element providing radially inward compression about said access element sufficient to increase the self-sealing ability of said access element without causing said base tubing element to collapse, wherein said compression element is a homogeneous continuous structure over substantially the entire length of said access element.

17. The self-sealing vascular graft of claim 16, wherein said biocompatible material for said base tubing element is or expanded polytetrafluorethylene; said biocompatible material for said access element is a platinum-cured gum silicone elastomer; and said biocompatible material for said compression element is a platinum cured silicone gum elastomer.

18. The self-sealing vascular graft of claim 17, wherein said access element has a wall thickness of about 0.33 mm to about 1.5 mm; and said compression element has a wall thickness of about 0.25 mm to about 0.55 mm, wherein the exterior surface of said compression element is microporous or textured.

* * * * *

UNITED STATES PATENT AND TRADEMARK OFFICE
CERTIFICATE OF CORRECTION

PATENT NO. : 8,163,002 B2
APPLICATION NO. : 11/517683
DATED : April 24, 2012
INVENTOR(S) : Steven Weinberg It is certified that error appears in the above-identified patent and that said Letters Patent is hereby corrected as shown below:

In the Specifications:

Column 3, Line 24 delete "then" and replace with --than--

Column 3, Line 56 "polyether or polycarbonate based" should read --polyether- or polycarbonate-based--

Column 4, Line 3 delete "two part" and replace with --two-part--

Column 4, Line 8 "surface of access" should read --surface of the access--

Column 4, Line 44 delete "a" and replace with --an--

Column 5, Line 49 delete "then" and replace with --than--

Column 5, Line 49 "by surgeon," should read --by the surgeon,--

Column 6, Line 21 delete "a" and replace with --as--

Column 6, Line 29 delete "two part" and replace with --two-part--

Column 7, Line 42 delete "polyether based" and replace with --polyether-based--

Column 7, Lines 42 and 43 delete "polycarbonate based" and replace with --polycarbonate-based--

Column 7, Lines 55 and 56 delete "polyether based" and replace with --polyether-based-- delete "polycarbonate based" and replace with --polycarbonate-based--

Column 8, Line 15 delete "platinum cured" and replace with --platinum-cured--

Column 8, Line 46 delete "or"

Signed and Sealed this
Twenty-third Day of July, 2013

Teresa Stanek Rea
*Acting Director of the United States Patent and Trademark Office*